(12) United States Patent
Iwata et al.

(10) Patent No.: US 6,627,399 B1
(45) Date of Patent: Sep. 30, 2003

(54) RNA POLYMERASE TRANSCRIPTION PROMOTERS AND NUCLEIC ACID SEQUENCING METHOD

(75) Inventors: Masaaki Iwata, Wako (JP); Yoshihide Hayashizaki, Tsukuba (JP)

(73) Assignee: Riken, Wako (JP)

( * ) Notice: Subject to any disclaimer, the term of this patent is extended or adjusted under 35 U.S.C. 154(b) by 0 days.

(21) Appl. No.: 09/622,644

(22) PCT Filed: Dec. 21, 1999

(86) PCT No.: PCT/JP99/07169

§ 371 (c)(1),
(2), (4) Date: Oct. 23, 2000

(87) PCT Pub. No.: WO00/37633

PCT Pub. Date: Jun. 29, 2000

(30) Foreign Application Priority Data

Dec. 21, 1998 (JP) .............................. 10-363297

(51) Int. Cl.[7] .......................... C12Q 1/68; C12N 15/10; A61K 7/11; C12P 19/34; C07H 21/02
(52) U.S. Cl. ....................... 435/6; 435/91.2; 424/70.17; 536/23.1; 536/24.1
(58) Field of Search ................... 435/6, 91.2; 536/24.1, 536/23.1; 424/70.17

(56) References Cited

U.S. PATENT DOCUMENTS 5,459,195 A * 10/1995 Longhi ................... 524/538
6,074,824 A * 6/2000 Hayashizaki et al. ........... 435/6

FOREIGN PATENT DOCUMENTS

| JP | 8-9997 | 1/1996 | ............ C12Q/1/68 |
| JP | 08009997 A | * 1/1996 | ............ C12Q/1/66 |

OTHER PUBLICATIONS

Sasaki et al, "Transcriptional sequencing: A method for DNA sequencing using RNA polynerase", National Academy of Science, vol. 95, pp. 3455–3460, (1998).*

Porter et al. Relative abilities of Bis(ethyl) derivatives of putrescine, spermidine, and spermine to regulate polyamine biosynthesis and inhibit L1210 Leukemia cell grouwth, Cancer Research, 1987, vol. 47, p. 2821–2825.*

Frugier et al., "Synthetic polyamines stimulate in vitro transcription by T7 RNA polymerase", Nucleic Acids Res., (1994), vol. 22, No. 14, p. 2784–2790.

Eichler et al., "Polyamine effects on DNA–directed RNA polymerases int he ciliate tetrahymena–thermophilla in–vivo and in–vitro experiments suggesting highly specific regulative interactions", Biol. Chem. Hoppe–Seyler (1989), vol. 370, No. 5, p. 451–466.

* cited by examiner

Primary Examiner—Gary Benzion
Assistant Examiner—Joyce Tung
(74) Attorney, Agent, or Firm—Burns, Doane, Swecker & Mathis, L.L.P.

(57) ABSTRACT

An RNA polymerase transcription accelerator comprising a compound represented by the following Formula (I) or salts thereof.

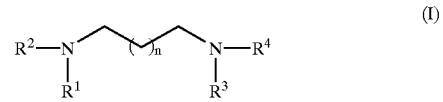

A method of sequencing DNA in which nucleic acid transcripts are obtained using an RNA polymerase and a DNA fragment as a template, the resulted nucleic acid transcripts are separated, the nucleic acid sequence is determined from the separated fractions wherein the nucleic acid transcription reaction is carried out in the presence of a compound selected from a group of compounds represented by the above formula (I).

The polyamine compounds above have outstanding accelerating activity on transcription activity of RNA polymerase. Therefore, use of the polyamine compounds in a DNA sequencing method using RNA polymerase can make a length of DNA sequence that can be determined in one sequencing longer.

3 Claims, No Drawings

RNA POLYMERASE TRANSCRIPTION PROMOTERS AND NUCLEIC ACID SEQUENCING METHOD

This application is A 371 of PCT/JP99/07169 filed Dec. 21, 1999.

TECHNICAL FIELD

The present invention relates to polyamine compounds which accelerate the transcription reaction of RNA polymerase (hereinafter referred to as RNAP). Further, the present invention relates to a DNA sequencing method using RNAP with the polyamine compounds and an initiator of nucleic acid transcription reaction by RNAP.

BACKGROUND TECHNOLOGY

A DNA sequencing method is one of the most important means in molecular biological field. One of the most useful nucleic acid sequencing method at present is a direct transcription sequencing method (WO96/14434) using RNAP such as T7 RNAP and a terminator of RNA transcription reaction (for example, 3'-deoxyribonucleotide-5'-triphosphate, 3'dNTPs). This method is an outstanding method utilizing the RNAP transcription reaction for sequencing nucleic acid sequences of DNA products amplified by polymerase chain reaction without removing primers and 2'-deoxyribonucleoside-5-triphosphates (2' dNTP's). Recently, it has been suggested that the RNAP transcripton can be improved by the addition of a compound.

Under the circumstances, it is hoped that a compound with RNAP promoting effect will be developed. It has been reported that as a transcription from DNA to mRNA proceeds, a concentration of natural polyamines increases in in vivo system (C. W. Tabor H. Tabor. Ann. Rev. Biochem. 53, 749–790(1984) and J. Marton and D. R. Morris, "Inhibition of Polyamine Metabolism", (P. P. McCann, A. E. Pegg, and A. Sjoerdsma, eds)). This report suggests that a natural polyamine participates in RNAP transcription process."

M. Flugier, C. Florentz, M. W. Hosseini, J. M. Lehn and R. Giege, Nucleic Acids Research, 22(14), 2784–2790 (1994) disclosed that the transcription activity of T7 RNAP is promoted by linear and cyclic synthetic polyamines. However, it is pointed out that the evaluation method of a transcription promoting ability in the report of M. Flugier et al has some problems. In fact, by using an evaluation method used by the present inventor, it has been found that polyamines described in the report have only extremely low accelerating effects. Therefore, the investigation of products having higher accelerating activity for RNAP transcription activity and an improvement of a sequencing method is highly desired.

SUMMARY OF THE INVENTION

An object of the present invention is to provide novel synthetic polyamine compounds with higher and outstanding accelerating activity for RNAP transcription activity than synthetic polyamines described in the state of the art, and to provide a method of DNA sequencing which can determine longer DNA sequences at a time by using the novel polyamine compounds which accelerate RNAP transcription activity.

The present invention relates to a RNA polymerase transcription accelerator comprising a compound represented by the general formula (I) below or a salt thereof.

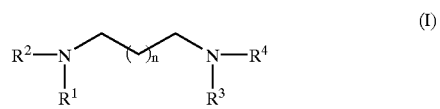

wherein,
n represents an integer from 1 to 8,
$R^1$ represents a hydrogen atom or p-toluenesulfonyl group,
$R^2$ represents an ethyl group or a group represented by the general formula (II),
$R^3$ represents a hydrogen atom or p-toluenesulfonyl group,
$R^4$ represents an ethyl group or a group represented by the general formula (II).

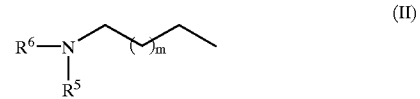

wherein,
m represents 1 or 2,
$R^5$ represents a hydrogen atom,
$R^6$ represents a hydrogen atom or an ethyl group.

Compounds 5, 10, 15a–g, and 18–23 described in the following Examples are represented by the above general formula (I). The relation between compounds 5, 10, 15a–g, and18–23, and the general formula (I) are shown in Table 1 below. In the table, No[a)] represents numbers of compounds in schemes below.

TABLE 1

Correlation between compounds 5, 10, 15a–g, and 18–23 and the general formula (I)

| No[a)] | $R^1$ | $R^2$ | $R^3$ | $R^4$ | $R^5$ | $R^6$ | N | m |
|---|---|---|---|---|---|---|---|---|
| 5 | H | formula (II) | H | formula (II) | H | Et | 2 | 1 |
| 10 | H | Et | H | formula (II) | H | Et | 1 | 2 |
| 15 | H | formula (II) | H | formula (II) | H | ET | a: 2<br>b: 3<br>c: 4<br>d: 5<br>e: 6<br>f: 7<br>g: 8 | 2 |
| 18 | H | Et | H | formula (II) | H | H | 1 | 2 |
| 19 | H | formula (II) | H | formula (II) | H | H | 6 | 2 |
| 20 | Ts | Et | Ts | Et | — | — | 6 | — |
| 21 | H | Et | H | Et | — | — | 6 | — |
| 22 | Ts | Et | Ts | Et | — | — | 3 | — |
| 23 | H | Et | H | Et | — | — | 3 | — |

H represents a hydrogen atom, and Et represents an ethyl group in the table.

Salts may be either inorganic or organic acid salts. The inorganic acid salts include hydrochlorides, bromates and the like. The organic acid salts include acetates, citrates and the like. Among these, bromates are preferred, but not limited thereto.

A method of DNA Sequencing Using RNA Polymerase Transcription Accelerator

The present invention relates to a method of DNA sequencing wherein nucleic acid transcripts are produced by using an RNA polymerase and a DNA fragment as a template, the resulted nucleic acid transcripts are separated, the nucleic acid sequence is determined from the separated fractions, characterized in that said nucleic acid transcription reaction is carried out in the presence of at least one compound selected from the group consisting of compounds represented by the above-mentioned general formula (I).

The method of sequencing DNA of the present invention is characterized in that the nucleic acid transcription reaction is carried out in the presence of at least one of RNA polymerase transcription accelerators of the present invention.

When about 0.5–5 mmol of at least one of these compounds to 1 unit of an RNA polymerase is coexisted in the nucleic acid transcription reaction using RNA polymerase, sequencing of longer strands can be possible even if the amount of RNA polymerase used is not increased. Further, the amount of RNA polymerase or a template used in the nucleic acid transcription reaction can be reduced by the use of the compound of the present invention when the lengths of the DNAs to be subjected are not to be elongated.

A method of DNA sequencing is described below. Methods of DNA sequencing in which nucleic acid transcripts are obtained by using RNA polymerase and a DNA fragment as a template, the resulted nucleic acid transcripts are separated, and the nucleic acid sequence is determined from the separated fractions are already publicly known. Moreover, a method for enzymatically synthesizing nucleic acid transcription products by RNA polymerase using a DNA fragment comprising a promoter sequence for the RNA polymerase, a method for separating nucleic acid transcription products, and a method for determination of nucleic acid sequence from separated fractions are also publicly known. Therefore, for these purposes, any known methods, conditions, and equipments can be suitably used in this invention.

There is no limitation to the DNA fragment used as a template except that it comprises a promoter sequence for RNA polymerase. For example, the DNA fragment comprising a promoter sequence can be a DNA product amplified by polymerase chain reaction. Further, a nucleic acid transcription generation reaction in the method of the present invention can be carried out without removal of a primer and/or 2'-deoxyribonucleoside-5'-triphosphate and/or derivatives thereof used in the polymerase chain reaction from the amplified DNA product. The polymerase chain reaction used for the above DNA amplification can be a method which is widely used as PCR method. Further, the DNA fragment comprising a promoter sequence may be a DNA fragment which has been cloned using an adequate host after ligating the promoter sequence and a DNA fragment to be amplified. That is, in the present, invention, there is no limitation to a DNA sequence to be amplified, a primer, and conditions for the amplification and the like.

The polymerase chain reaction for the amplification of the DNA fragment comprising a promoter sequence can be performed, for example, in a 20 µl volume of solution containing 10–50 ng of genomic DNA or 1 pg of cloned DNA, 10 µM of each primer, and 200 µM of each 2'-deoxyribonucleoside-5'-triphosphate (dATP, dGTP, dCTP, dTTP) using a DNA polymerase such as a Taq polymerase.

Provided that, either one of primers for the polymerase chain reaction, or an insert DNA amplified is required to have a promoter sequence for RNA polymerase, which will be described hereinafter. In the direct transcription sequencing method, two types of primers, one of which has a phage promoter sequence, are used in the PCR amplification, or an amplified insert DNA having a phage promoter sequence is used. As a result, the resulted PCR products can be subjected to an in vitro transcription using RNA polymerase which is activated by the above promoter sequence.

The promoter sequence for the RNA polymerase can be appropriately selected in view of the RNA polymerase to be used.

In the method of the present invention, a nucleic acid transcript such as an RNA transcript is synthesized from a DNA fragment comprising a promoter sequence. Since the DNA fragment comprises a promoter sequence for RNA polymerase, recognition of this promoter sequence by the RNA polymerase enables to synthesize the nucleic acid transcript such as an RNA transcript.

Nucleic acid transcripts such as RNA transcripts can be Synthesized by reacting, for example, ribonucleoside-5'-triphosphates (NTPs) such as ATP, GTP, CTP and UTP or derivatives thereof (provided that, one of the NTPs may be a compression suppressed ribonucleotide derivative) and one or more 3'dNTP derivatives in the presence of the above-mentioned nucleic acid transcription initiator and the RNA polymerase. The term "3' dNTP derivative" is herein used as a generic term for indicating 3' dATP, 3' dGTP, 3' dCTP, 3' dUTP and derivatives thereof. At least four kinds of ribonucleoside-5-triphosphates (NTPs) each having a different nucleic acid are necessary for a synthesis of a transcript even if a part of the NTP such as ATP is a derivative.

When 3' dNTP derivative is incorporated into the 3' end of the transcription product such as RNA or nucleic acids, the synthesis of RNA or nucleic acid is interfered due to lack of 3' hydroxy group. As a result, RNAs or nucleic acid fragments with various lengths in which a 3' dNTP derivative has been incorporated into their 3' ends are generated. With respect to each of four 3' dNTP derivatives each having a different nucleic acid, such ribonucleoside analogues are produced. Upon preparation of four ribonucleoside analogues, determination of RNA or nucleic acid sequence can be done [Vladimir D. Axelred et al. (1985) Biochemistry Vol. 24, 5716–5723].

One or more of the 3' dNTP derivatives can be used in a nucleic acid transcription reaction. When the nucleic acid transcription reaction is performed using only one of 3' dNTP derivatives, four kinds of transcription products each having at the 3' end a 3' dNTP derivative different in nucleic acid are obtained by carrying out nucleic acid transcription reaction four times. Through one nucleic acid transcription reaction, a transcription product comprising a mixture of various RNAs or nucleic acid fragments having the same 3' dNTP derivative at the 3' end and different molecular weight is produced. The resulted four kinds of transcription products can be independently subjected to separation and sequence determination described below. Alternatively, two or more of four transcription products are mixed and the resulted mixture can be subjected to separation and sequence determination.

When two or more of 3' dNTP derivatives are used for one nucleic acid transcription reaction at once, a reaction product containing two or more transcription products each having at the 3' end a 3' dNTP derivative different in nucleic acid can be obtained. This product can be subjected to separation and sequence determination described below. It is preferred to use 2 or more 3' dNTP derivatives for a nucleic acid transcription reaction at once, because the number of nucleic acid transcription reaction procedures can be reduced.

Further, transcription of nucleic acid such as RNA is carried out by using RNA polymerase in the presence of four ribonucleoside-5'-triphosphates each having different nucleic acid and is terminated by the 3' dNTP derivatives. As a result, with respect to each nucleic acid, RNA or nucleic acid ladder can be produced for sequencing. In particular, in the present invention, it is preferred to carry out the nucleic acid transcription in the presence of four ribonucleoside-5'-triphosphates each having a different nucleic acid, separation of the resulted transcription products and determination of four nucleic acid sequences at once.

RNA Polymerase

The RNA polymerase used in the method of the present invention can either be a wild-type RNA polymerase and a mutant RNA polymerase. The RNA polymerase is preferably a mutant RNA polymerase wherein at least one amino acid has been modified to have higher 3' dNTP derivatives incorporation ability than that of the wild-type RNA polymerase. The "wild-type RNA polymerase" herein includes all naturally occurred RNA polymerases, and a modified wild-type RNA polymerase which has substitution, insertion or deletion of amino acids which are not the modification for obtaining increased incorporation ability of 3'-deoxyribonucleotide or its derivatives compared to that of the corresponding wild-type RNA polymerase. That is, wild-type RNA polymerases artificially modified with a purpose other than that described above are included in the above "wild-type RNA polymerase". However, it is suitable make sure that such a substitution, insertion or deletion of amino acids to the extent that activity of RNA polymerase is maintained.

Examples of the "wild-type RNA polymerase" include RNA polymerase derived from T7 phage, T3 phage, SP6 phage, and K11 phage. However, it is not limited to these RNA polymerases.

The "wild type RNA polymerase" according to the present invention includes naturally occurring thermostable RNA polymerases, and naturally occurring RNA polymerases artificially modified (i.e. having substitution, insertion and/or deletion of amino acids) in order to impart thermostablity. However, it is suitable to make the modification for imparting thermostablity to the extent that the activity of RNA polymerase is maintained. The mutant RNA polymerase of the present invention prepared by using a thermostable RNA polymerase as the "wild type RNA polymerase" shall be thermostable. As a result, for example, it can be used in PCR to synthesize RNA fragments for sequencing in situ, i.e., during PCR, by using the PCR product as a template.

T7 RNA polymerase has been known to be a promoter specific RNA polymerase with an extremely high specificity. The nucleotide sequence and production method of T7 RNA polymerase are reported in Davanloo et al., Proc. Natl. Acad. Sci. USA., 81:2035–2039 (1984). Its large-scale production has been already described in Zawadzki et al., Nucl. Acids Res., 19:1948 (1991). This phage-derived RNA polymerase can pursue the transcription reaction with a single polypeptide, unlike RNA polymerases of *E. coli* and higher organisms (Chamberlin et al., Nature, 228:227–231,1970). Therefore, it is a particularly excellent material for analyzing the mechanism of transcription, and many mutants have been isolated and reported. Further, the results of its crystallographic analysis are mentioned in Sousa et al., Nature, 364:593–599, 1993.

As other promoter specific RNA polymerases of high specificity, 3 kinds of RNA polymerases derived from T3 phage which infects *E. coli*, SP6 phage which infects Salmonella, and K11 phage which infects *Klebsiella pneumoniae* have been well known.

The four kinds of RNA polymerases mentioned above are quite similar to one another in their primary structure of amino acids, sequence of promoter and the like as described hereinafter.

The above-modified RNA polymerase has an increased ability of incorporating 3'-deoxyribonucleotides and derivatives thereof in comparison with the ability of a corresponding wild type RNA polymerase. Wild type RNA polymerases poorly incorporate 3'-deoxyribonucleotides in comparison with ribonucleotides, which has obstructed their use in nucleotide sequencing. In contrast, the modified RNA polymerase has the ability of incorporating 3'-deoxyribonucleotides and derivatives thereof at least twice higher than that of wild type. The incorporation of 3'-deoxyribonucleotides tends to be decreased especially when 3'-deoxyribonucleotide derivatives are labeled with a fluorescent tag. The modified RNA polymerase can also improve incorporation of such 3'-deoxyribonucleotide derivatives.

A mutated or mutant RNA polymerase is a polymerase of which at least one of amino acids in a corresponding wild type RNA polymerase has been modified. Such modification of an amino acid may be not only substitution of amino acid but also insertion or deletion of amino acid. The mutation of amino acid is, for example, substitution of tyrosine for at least one amino acid residue in a naturally occurring amino acid sequence. The amino acid to be replaced may be, for example, phenylalanine. However, the amino acid to be replaced is not limited to phenylalanine, and any amino acid may be replaced so long as it can enhance the ability for incorporating 3'-deoxyribonucleotides and other ribonucleotide analogues relative to ability for the corresponding ribonucleotides.

Example of the mutant RNA polymerase includes mutant T7. RNA polymerase F644Y and L665P/F667Y. The numbers indicate an amino acid number counting from the N terminal of the polymerase protein. For example, F667 means that the amino acid residue No. 667 is F, and F667Y means that the amino acid residue F No. 667 is Y substituted by F. These sustain the RNA synthesis activity sufficiently and have an improved ability for incorporating 3' dNTPs. The strong bias observed in the wild-type has been considerably decreased. Use of T7 RNA polymerase F644Y or L665P/F667Y having such characteristics enables a nucleotide sequence determination method utilizing transcription products, which is of more excellent practical applicability in comparison with a nucleotide sequence determination method utilizing a DNA polymerase.

*E. coli* strains pT7RF644Y (DH5α) and pT7RL665P/F667Y (DH5 α), which produce the mutant T7 RNA polymerases F644Y and L665P/F667Y respectively, were already deposited at the National Institute of Bioscience and Human-Technology with international deposition numbers of 5998 (FERM-BP-5998) and 5999 (FERM-BP-5999) respectively on Jul. 2, 1997.

The aforementioned mutant RNA polymerases can be produced by preparing a nucleic acid molecule encoding a RNA polymerase, introducing a mutation into the nucleic acid molecule so that one or more nucleotides in one or more regions should be mutated, and collecting a modified RNA polymerase expressed by the mutated nucleic acid molecule. Preparation of the nucleic acid molecule encoding RNA polymerase, introduction of mutation into the nucleic acid molecule, and collection of the modified RNA polymerase can be performed by using conventional methods.

For example, a mutant T7 RNA polymerase can be constructed by the following method. By using an expression vector inserted with a T7 RNA polymerase gene as template, an expression plasmid comprising a region between the HpaI, and NcoI restriction sites in the C-terminus side of T7 RNA polymerase gene which is introduced with a mutation by PCR is constructed. Subsequently, this expression plasmid can be transformed into *E. coli* DH5 α, which can then produce a large amount of a mutant T7 RNA polymerase protein upon addition of isopropyl-β-D-thiogalactopyranoside (IPTG)

Inorganic Pyrophosphatase

In the method of the present invention, a nucleic acid transcription generation reaction is preferably performed in the presence of inorganic pyrophosphatase. With the use of inorganic pyrophosphatase, stable sequence data can be obtained since bias to incorporation ability can be cancelled. The bias is such that incorporation of 3'-deoxyribonucleotide and the derivatives thereof into a polyribonucleotide sequence is difficult compared to corresponding ribonucleotide and incorporation into the sequence varies depending on the kind of nucleic acid among ribonucleotides and 3'-deoxyribonucleotides. That is, it decreases differences in peak altitudes (intensities of signals) corresponding to each labeled ribonucleotide, thereby precision of sequence determination is improved and it makes possible to obtain more accurate sequencing data.

Pyrophosphorolysis occurs due to increase of pyrophosphate produced by DNA synthesis, and it acts to promote the reaction so that the resulting DNA product should be decomposed. As a consequence, the pyrophosphorolysis inhibits the sequencing in the dideoxy sequencing method utilizing a DNA polymerase. As for this fact, it has been known that, when an inorganic pyrophosphatase is used in the dideoxy sequencing method utilizing a DNA polymerase, it inhibits the pyrophosphorolysis and thus affords stable sequencing data [Japanese Patent Unexamined Publication (KOKAI) No. Hei 4-506002/1992].

The pyrophosphorolysis is also effective in the sequencing method utilizing an RNA polymerase. More stable sequence data can be obtained by performing the nucleic acid transcription reaction in the presence of inorganic pyrophosphatase since differences in peak altitudes (intensities of signals) corresponding to each labeled ribonucleotide can be reduced.

Inorganic pyrophosphatase (EC.3.6.1.1) is commercially available, and for example, it is sold by Sigma as INORGANIC PYROPHOSPHATASE and by Boehringer as Pyrophosphatase. While the amount of inorganic pyrophosphatase to be used may depends on the degrees of activities of inorganic pyrophosphatase and RNA polymerase, it is suitably in the range of $10^{-6}$ to $10^{-2}$ units for 1 unit of RNA polymerase.

Compression Suppression Ribonucleotide Derivatives

In the present invention, it is preferred to use a compression suppression ribonucleotide derivative in a nucleic acid transcription reaction, so that compression can be suppressed and precision of sequencing determination can be improved. Accuracy of the sequencing determination can be improved by suppressing the compression.

The compression suppression ribonucleotide derivatives are ribonucleotide derivatives that can suppress compression in sequencing analysis. The compression suppression ribonucleotide derivatives can be selected from, for example, ribonucleotides with base (nucleic acid) analogues instead of bases (nucleic acids). The base analogues can be either natural compounds or synthetic compounds. The synthetic compounds include, for example, those in which some carbon atoms constituting a purine ring or a pyrimidine ring are substituted by nitrogen atoms or those in which some nitrogen atoms constituting a purine ring or a pyrimidine ring are substituted by carbon atoms. Alternatively, it can be a compound in which various substituents are introduced into its purine or pyrimidine ring.

Examples of the compression suppression ribonucleotide derivatives, ribonucleotides having base analogues, include deazaribonucleoside-5'-triphosphates. Moreover, the deazaribonucleoside-5'-trophosphates include 7-deazaribonucleoside-5'-triphosphates and 3-deazaribonucleoside-5'-triphosphates. 7-deazaribonucleoside-5'-triphosphates include 7-deazaATP, 7-deazaGTP and derivatives thereof, and 3-deazaribonucleoside-5'-triphosphates include 3-deazaCTP, 3-deazaUTP and derivatives thereof.

Other Examples of the compression suppression ribonucleotide derivatives include deaminoribonucleoside-5'-triphosphates. An amino group is present in bases of ribonucleoside except for uracil. Each GTP, ATP and CTP has an amino group on $2^{nd}$ position of a purine ring, $6_{th}$ position of purine ring and $4_{th}$ position of pyrimidine ring respectively. The above-mentioned deaminoribonucleoside-5'-triphosphates are ribonucleotides in which the amino groups are decomposed, for example, $N^2$-deaminoGTP, $N^6$-deaminoATP and $N^4$-deaminoCTP, and derivatives thereof. Further, $N^2$-deaminoguanine is the same substance to inosine, and $N^2$-deaminoGTP may be abbreviated as ITP.

The other examples of the compression suppression ribonucleotide derivatives include derivatives having substituted 1 or 2 hydrogen atoms of amino group present in bases of ribonucleotides by organic groups except that hydrogen atoms. Examples of such derivatives are N-alkyl substituted ribonucleoside-5'-triphosphates (provided that an alkyl is a lower alkyl with carbon atom number 1–6, and the substitution is mono- or di-substitution). Provided that, the substituent can be selected from other organic groups except an alkyl group. Examples of ribonucleoside-5'-triphosphates substituted by N-alkyl are GTP substituted by $N^2$-monomethyl, CTP substituted by $N^4$-monomethyl, ATP substituted by $N^6$-monomethyl and derivatives thereof.

In a nucleic acid transcription reaction, the compression suppression ribonucleotide derivative can be used instead of ribonucleoside-5'-triphosphates for bases which easily form compression selected from four ribonucleoside-5'-triphosphates such as ATP, GTP, CTP and UTP or derivatives thereof. The compression suppression ribonucleotide derivatives can be used for 2 or more ribonucleoside-5'-triphosphates, if desired.

A deazaribonucleoside-5'-triphosphate can be used as compression suppression ribonucleotide derivative for one of four ribonucleoside-5'-triphosphates are [7-deazaATP, GTP, CTP, UTP], [ATP, 7-dezaGTP, CTP, UTP], [ATP, GTP, 3-deazaCTP, UTP], and [ATP, GTP, CTP, 3-deazaUTP]. The deaza NTP can be substituted by other compression suppression ribonucleotide derivatives. Compression suppression ribonucleotide derivatives such as 7-deazaNTPs are commercially available. It is also possible to use together 2 or more compression suppression ribonucleotide derivatives, or to use together both a compression suppression ribonucleotide derivative and a usual ribonucleoside-5'-triphosphate for the same nucleic acid.

When compression suppression ribonucleotide derivatives are used in place of a part of or all ribonucleoside-5'-triphosphates which are GTP or derivatives thereof, it is appropriate to use together guanosine, guanosine-5'-monophosphate (GMP) guanosine-5'-diphosphate (GDP), oligoribonucleotides represented by the general formula $N^1(N)_{n-1}G$ or oligoribonucleotides represented by the general formula $N^2(N)_{n-1}G$ together. In this case, the above-mentioned compression suppression ribonucleotide derivatives can be, for example, 7-deazaGTP, $N^2$-deaminoGTP or $N^2$-monomethyl substituted GTP.

When the compression suppression ribonucleotide derivatives are used in place of a part of or all ribonucleoside-5'-triphosphates which are ATP or derivatives thereof, it is appropriate to use together adenosine, adenosine-5'-monophosphate (AMP), adenosine-5'-diphosphate (ADP), oligoribonucleotides represented by the general formula $N^1(N)_{n-1}A$ or oligoribonucleotides represented by the general formula $N^2(N)_{n-1}A$. In this case, the compression suppression ribonucleotide derivatives can be, for example, 7-deazaATP, $N^6$-deaminoATP or $N^6$-monomethyl substituted ATP.

When compression suppression ribonucleotide derivatives are used in place of a part of or all ribonucleoside-5'-triphosphates which are CTP or derivatives thereof, it is appropriate to use together cytidine, cytidine-5'-monophosphate (CMP), cytidine-5'-diphosphate (CDP), oligoribonucleotides represented by the general formula $N^1(N)_{n-1}C$ or oligoribonucleotides represented by the general formula $N^2(N)_{n-1}C$. In this case, the compression suppression ribonucleotide derivatives can be, for example, 3-deazaCTP, $N^4$-deaminoCTP or $N^4$-monomethyl substituted CTP.

When compression suppression ribonucleotide derivatives are used for some or all ribonucleoside-5'-triphosphates which are UTP or derivatives thereof, it is appropriate to use together uridine, uridine-5'-monophosphate (UMP), uridine-5'-diphosphate (UDP), oligoribonucleotides represented by the general formula $N^1(N)_{n-1}U$ or oligoribonucleotides represented by the general formula $N^2(N)_{n-1}U$ together. In this case, the compression suppression ribonucleotide derivatives can be, for example, 3-deazaUTP, $N^2$-deaminoUTP or $N^2$-monomethyl substituted UTP.

Nucleic Acid Transcription Initiator

In a nucleic acid transcription reaction of the method of the present invention, it is preferred to use together the above-mentioned compression suppression ribonucleotide derivatives and nucleic acid transcription initiator from the viewpoint of easy start of nucleic acid transcription reaction. The nucleic acid transcription initiator can be selected from, for example, ribonucleoside, ribonucleoside-5'-monophosphate, ribonucleoside-5'-diphosphate, oligoribonucleotides represented by the general formula $N^1(N)_n$ (wherein, $N^1$ represents ribonucleoside, ribonucleoside-5'-monophosphate or ribonucleoside-5'-diphosphate, N represents ribonucleoside-5'-mono phosphate and n represents an integer of 1 or more) and oligoribonucleotides represented by the general formula $N^2(N)_n$ (wherein $N^2$ represents a group represented by a formula (1) below, N show ribonucleoside-5'-monophosphate and n represents an integer of 1 or more).

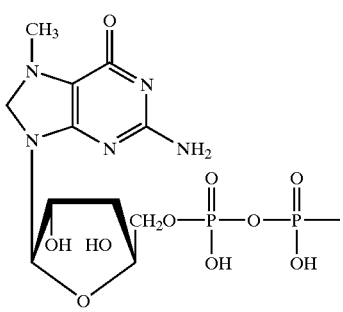

(1)

More specific examples of the nuclei& acid transcription initiator include guanosine, guanosine-5'-monophosphate (GMP), guanosine-5'-diphosphate (GDP), oligoribonucleotides represented by the general formula $N^1(N)_{n-1}G$ (provided that, $N^1$ represents ribonucleoside, ribonucleoside-5'-monophosphate, or a ribonucleoside-5'-diphosphate, N represents a ribonucleoside-5'-monohosphate, n represents an integer of 1 or more, G represents guanosine-5'-monophosphate) and oligoribonucleotides represented by the general formula $N^2(N)_{n-1}G$ (wherein, $N^2$ represents a group represented by the formula (1) N represents a ribonucleoside-5'-monohposphate, n represents an integer of 1 or more, G represents guanoside-5'-monophosphate).

Further, more specific examples of the nucleic acid transcription initiator include adenosine, adenosin-5'-monophosphate (AMP), adenosine-5'-diphosphate (ADP), oligoribonucleotides represented by the general formula $N^1(N)_{n-1}A$ (provided that, $N^1$ represents a ribonucleoside, a rionucleoside-5'-monophosphate, or a ribonucleoside-5'-diphosphate, N represents a ribonucleoside-5'-monophosphate, n represents an integer of 1 or more, and A represents an adenosine-51'-monophosphate), and oligoribonucleotides represented by the general formula $N^2(N)_{n-1}A$ (wherein, $N^2$ represents a group represented by the formula (1) below, N represents ribonucleoside-5'-monophosphate, n represents an integer of 1 or more, and A represents adenosine-5'-monophosphate).

More specific examples of the nucleic acid initiator include cytidine, cytidine-5'-monophosphate (CMP), cytidine-5'-diphosphate (CDP), oligoribonucleotides represented by the general formula $N^1(N)_{n-1}A$ (provided that, $N^1$ represents a ribonucleoside, a ribonucleoside-5'-monophosphate or a ribonucleoside-5'-diphosphate, N represents, a ribonucleoside-5'-monophosphate, n represents an integer, of 1 or more, C represents cytidine-5'-monophosphate) and oligoribonucleotides represented by the general formula $N^2(N)_{n-1}C$ (wherein, $N^2$ represents a group represented by formula (1) below, N represents a ribonucleoside-5'-monophosphate, n represents an integer of 1 or more, and C represents cytidine-5'-monophosphate).

Further, more specific examples of the nucleic acid transcription initiator include uridine, uridine-5'-monophosphate (UMP), uridine-5'-diphosphate (UDP) oligoribonucleotides represented by the general formula $N^1(N)_{n-1}U$ (provided that, $N^1$ represents a ribonucleoside, a ribonucleoside-5'-monophosphate or a ribonucleoside-5'-diphosphate, N represents a ribonucleoside-5'-monophosphate, n represents an integer of 1 or more, U represents an uridine-5-monophosphate) and oligoribonucleotides represented by the general formula of $N^2(N)_{n-1}U$ (wherein, $N^2$ represents a group represented by formula (1) below, N represents a ribonucleoside-5'-monophosphate, n represents an integer of 1 or more, U represents uridine-5'-monophosphate).

The bases (nucleic acids) of the ribonucleosides, ribonucleoside-5'-monophosphates and ribonucleosides-5'-diphosphates represented by $N^1$ in the above-mentioned general formulas $N^1(N)_n$, $N^1(N)_{n-1}G$, $N^1(N)_{n-1}A$, $N^1(N)_{n-1}C$, $N^1(N)_{n-1}U$, $N^2(N)_n$, $N^2(N)_{n-1}G$, $N^2(N)_{n-1}A$, $N^2(N)_{n-1}C$, $N^2(N)_{n-1}U$ are not specially limited, and can be suitably selected from guanine, adenine, cytosine, and uridine. Further, bases of ribonucleoside-5'-monophosphates represented by N and nucleic acid sequence in which n is 2 or more are not specially limited. Moreover, n is not limited by a function of an initiator, however, according to a commercial availability, n is practically around 10 or less, preferably 5 or less.

Separation and Determination of Nucleic Acid Transcription Products

In the method of the present invention, a nucleic acid transcription product is separated. The separation can be suitably performed by any method which enables the separation of numerous product molecules having different molecular weight, included in the transcription products according to the molecular weight. Examples of such methods include electrophoresis. HPLC can also be used.

Conditions of electrophoresis and the like are not particularly limited and it can be carried out in a conventional manner. The sequence of RNA or nucleic acid can be determined from bands (nucleic acid ladder) provided by subjecting the transcription products to electrophoresis.

Detection of RNA nucleic acid ladder can be done by, for example, labeling terminators, ribonucleoside-5'-tirophosphates (NTPs), used for transcript reaction. When the nucleic acid transcription initiator is used, it can be performed by labeling the nucleic acid transcription initiator. Detection of RNA or nucleic acid ladder can also be performed by labeling 3' dNTP derivatives used in the transcript reaction. The labeling can be, for example, florescence, or radioactivity or stable isotope, and florescence is preferred from safety and manipulation reasons. Further, it is also possible to determine sequence of the transcription products separated by electrophoresis by measuring mass of each transcription reaction products with a mass spectrometer without using the above-mentioned labeling.

In particular, sequence of the transcription products can be determined, for example, by using labeled 3' dNTP such as labeled 3' dATP, 3' dGTP, 3' dCTP, and 3' dUTP, subjecting the transcription products to electrophoresis and detecting radioactivity or stable isotope, or florescence from the resulted bands. The detection can easily be performed by labeling 3' dNTP derivatives as mentioned above since differences in radioactivity or florescence intensities between the bands can be eliminated. Further, detection of ladders which generate radioactivity or stable isotope, or florescence can be carried out by using a usual apparatus for DNA sequencing.

Sequence of the transcription products can also be determined by using ATP, GTP, CTP and UTP labeled with radioactivity or stable isotope, or florescence and detecting the radioactivity or stable isotope, or florescence of bands of electrophoresis.

Further, RNA or nucleic acid sequence can be determined by using 3' dATP, 3' dGTP, 3' dCTP and 3' dUTP each labeled with a different florescence and detecting four types of florescence from the bands obtained by electrophoresis in which a mixture of various transcription product fragments each having 3' dATP, 3' dGTP, 3' dCTP or 3' dUTP at it end and each having a different florescence are separated each other.

In this method, four kinds of 3' dNTPs are labeled with a different florescence. Thus, by subjecting a mixture of four kinds of transcription products each having a different 3' end to electrophoresis, bands generating florescence corresponding to the four different kinds of 3' dNTP at the 3' end can be obtained and RNA or nucleic acid sequence can be determined with respect to four nucleic acids at once by distinguishing the difference of florescence.

3'-deoxyribonucleotide derivatives described in WO96/14434 and Japanese Patent Laid-open Showa No. 63-152364 can be used as the florescence labeled 3' dNTPs. Further, florescence labels are preferred to be florescence dyes which generate detectable luminescence radiation by stimulation of energy absorption from a suitable supplying source such as an argon laser.

A DNA sequence used as a template of transcription can be determined from RNA or nucleic acid sequence determined by the above-mentioned method. When ladders for each nucleic acid are formed, the DNA sequence used as a template of the transcription can be determined by integrating RNA or nucleic acid information obtained from four kinds of ladders. Further, when ladders for two or more nucleic acids are formed at once (in which two or more base bands are present in the same ladder), the DNA sequence used as a template of transcription can be determined by integrating RNA or nucleic acid sequence information obtained from each ladder. In particular, when ladders for four bases (nucleic acid) are formed at once (in which bands for four kinds of nucleic acids are present in the same ladder), the DNA sequence used as a template of transcription can be determined from RNA or nucleic acid sequence information obtained from the single ladder.

EXAMPLES

Synthesis of Polyamine Compounds

The followings are a list of references for a method of polyamine compounds synthesis.

1) Iwata, Yamamoto and Nakajima, Japanese Patent Laid-open No. 08–027129 (Publication Date: Jan. 30, 1996), "Cyclic polyamine and antiviral agent containing the same as active ingredient"
2) Iwata and Kuzuhara, Japanese Patent No. 1857707, "Method for producing N-alkylformamide"
3) Iwata and Kuzuhara, Japanese Patent No. 1857749, "Polyamine derivative"
4) Iwata and Kuzuhara, Japanese Patent No. 1998558, "Method for producing polyamine derivatives"
5) Iwata and Kuzuhara, Japanese Patent No. 2123326 "N-phthalimide derivative and method for producing the same"
6) M. Flugier, C. Florentz, M. W. Hosseini, J. M. Lehn, and R.
Giege, Nucleic Acids Research, 22(14), 2784 2790(1994)

Example 1

Synthesis of 1,12-di(ethylamino) 4,9-diazadodecane HBr salt (5)

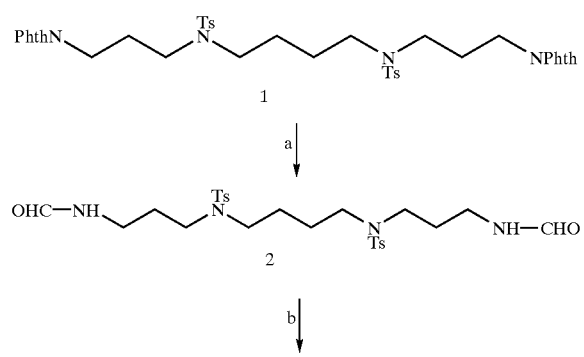

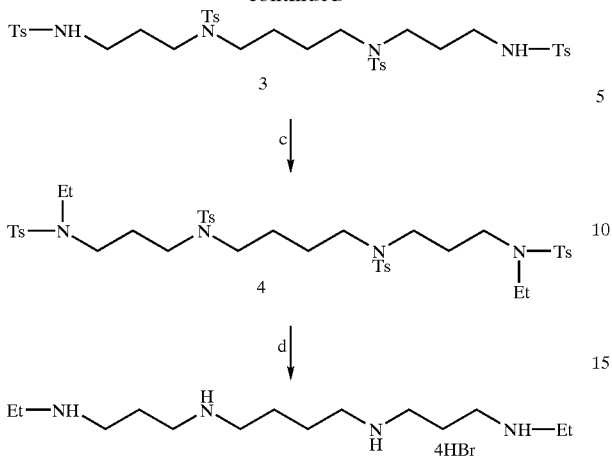

a N₂H₄/DMF 70° C. 1 d, b; 1.2N-HCl 70° C. 1 h, 2. TsCl/Py/NEt₃ rt 4 h, cEt—Br/ K₂CO₃/DMF d 33%-HBr—AcOH

[Phth = phthaloyl,
Ts = p-toluenesulfonyl,
Et = ethyl,
DMF = N,N-dimethylformamide,
AcOH = acetic acid]

Diaminobutane as a raw material was reacted with tosyl chloride at room temperature for 3 hours to obtain N1,N4-di(p-toluenesulfonyl)-1,4-diaminobutane. Using the obtained N1,N4-di(p-toluenesulfonyl)-1,4-diaminobutane and N-(3-bromopropyl)phthalimide as Chain A and Chain B, respectively, N1,N4,N9,N12-tetra(p-toluenesulfonyl)-1,12-diamino-4,9-diaz adodecane (3) was derived from the above Chain A and Chain B according to the known methods (Patent Documents 1 to 5 and References 6) Specifically, Compound 1 was synthesized, and then this Compound 1 was reacted with N₂H₄ in DMF at 70° C. for 1 day to obtain Compound 2. The obtained Compound 2 was first treated with 2N HCl at 70° C. for 1 hour, and then reacted with TsCl in pyridine in the presence of NEt₃ at room temperature for four hours to obtain Compound 3.

Subsequently, a mixture of the above Compound 3 (0.17 g), anhydrous potassium carbonate (0.143 g) and bromoethane (57 mg) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N4,N9,N12-tetra(p-toluenesulfonyl)-1,12-di(ethylamino)-4,9-diazadodecane (4, 0.106 g, yield:58%). The results of elementary analysis of Compound 4 are shown in Table 2 below, and the results of ¹H-NMR and ¹³C-NMR of the same are shown Table 4below, respectively. The obtained Compound 4 (96 mg) was heated with phenol (0.206 g) in 33% HBr in acetic acid (10 ml) with, stirring on an oil bath at75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 5 (see Scheme 1) as colorless powder.

Example 2

Synthesis of 1,8-di(ethylamino)-4-azaoctane HBr salt (10)

Scheme 2

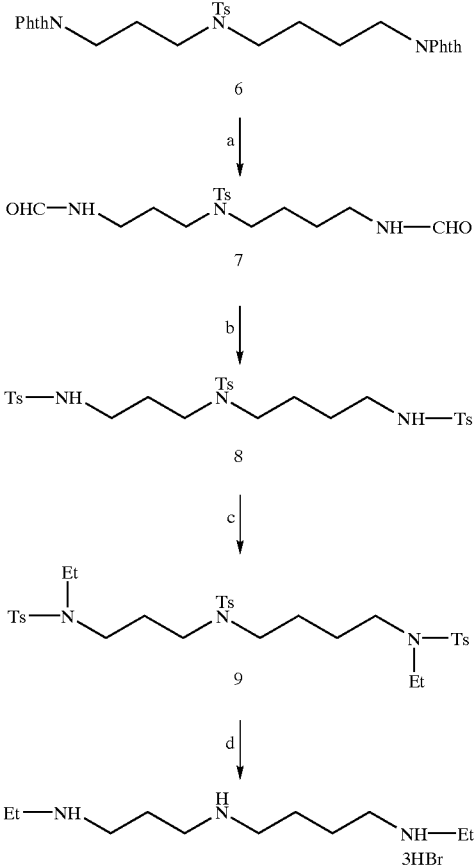

a N₂H₄/DMF 70° C. 1d, b; 1.2N-HCl 70° C. 1h, 2. TsCl/Py/NEt₃ rt 4h, c Et-Br/K₂CO₃/DMF d 33%-HBr-AcOH

3-Bromopropylamine as a raw material was reacted with tosyl chloride at 0° C. for 2 hours to synthesize N-(p-toluenesulfonyl)-3-bromopropylamine. Further, this was reacted with phthalimide at room temperature for 3 days to obtain N-(N3-p-toluenesulfonyl-3-aminopropyl)phthalimide. Using the obtained N-(N3-p-toluenesulfonyl-3-aminopropyl)phthalimide and N-(4-bromobutyl)phthalimide as Chain A and Chain B, respectively, N1,N4,N8-tri(p-toluenesulfonyl)-1,8-diamino-4-azaoctane (8) was derived from the above Chain A and Chain B according to the known methods (Patent Documents 1 to 5 and References 6). Specifically, Compound 6 was synthesized, and then this Compound 6 was reacted with N₂H₄ in DMF at 70° C. for 1 day to obtain Compound 7. The obtained Compound 7 was first treated with 2 N HCl at 70° C. for 1 hour, and then reacted with TsCl in pyridine in the presence of NEt₃ at room temperature for 4 hours to obtain Compound 8.

Subsequently, a mixture of the above Compound 8 (0.157 g), anhydrous potassium carbonate (0.178 g) and bromoethane (48 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art.

7734, 70–230 mesh) using chloroform:acetone (95:5 v/v) as a developing solvent to obtain N1,N4,N8-tri(p-toluenesulfonyl)-1,8-di(ethylamino)-4-azaoctane (Compound 9, 0.111 g, yield: 65%). The results of elementary analysis of Compound 9 are shown in Table 2 below, and the results of $^1$H-NMR and $^{13}$C-NMR of the same are shown in Table 4 below, respectively. The obtained Compound 9 (100 mg) was heated with phenol (0.283 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 10 (see Scheme 2) as colorless powder.

Example 3.1

Synthesis of 1,14-di(ethylamino)-5,10-diazatetradecane HBr salt (15b)

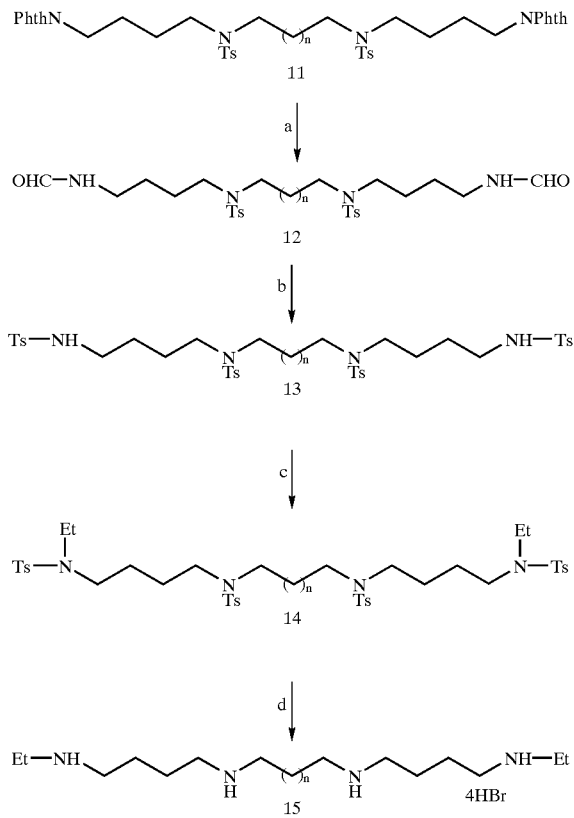

a N$_2$H$_4$/DMF 70° C. 1d, b; 1.2N-HCl 70° C. 1h, 2. TsCl/Py/NEt$_3$ rt 4h, c Et-Br/K$_2$CO$_3$/DMF d 33%-HBr-AcOH $$\begin{bmatrix} a\ n = 1, b\ n = 2, c\ n = 3, \\ d\ n = 4, e\ n = 5, f\ n = 6, \\ g\ n = 7, h\ n = 8 \end{bmatrix}$$

Diaminobutane as a raw material was reacted with tosyl chloride at room temperature for 3 hours to obtain N1,N4-di(p-toluenesulfonyl)-1,4-diaminobutane. Using the obtained N1,N4-di(p-toluenesulfonyl)-1,4-diaminobutane and N-(4-bromobutyl)phthalimide as Chain A and Chain B, respectively, N1,N5,N10,N14-tetra(p-toluenesulfonyl)-1,14-diamino-5,10-diazatetradecane (13b) was derived from the above Chain A and Chain B according to the known methods (Patent Documents 1 to 5 and References 6). Specifically, Compound 11a was synthesized, and then this Compound 11a was reacted with N$_2$H$_4$ in DMF at 70° C. for 1 day to obtain Compound 12a. The obtained Compound 12a was first treated with 2 N HCl at 70° C. for 1 hour, and then reacted with TsCl in pyridine in the presence of NEt$_3$ at room temperature for 4 hours to obtain Compound 13a.

Subsequently, a mixture of the above Compound 13a (0.179 g), anhydrous potassium carbonate (0.146 g) and bromoethane (40 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N10,N14-tetra(p-toluenesulfonyl)-1,14-di(ethylamino)-5,10-diazatetradecane (Compound 14a, 0.215 g, yield: 88;%). The results of elementary analysis of Compound 14b are shown in Table 4 below, and the results of $^1$H-NMR and $^{13}$C-NMR of the same are shown in Table 8 below, respectively. The obtained Compound 14a (114 mg) was heated with phenol (0.238 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15a (see Scheme 3) as colorless powder.

Example 3.2

Synthesis of 1,15-di(ethylamino)-5,11-diazapentadecane HBr salt (15b) (Scheme 3)

Diaminopentane as a raw material was reacted with tosyl chloride to obtain N1,N5-di(p-toluenesulfonyl)-1,5-diaminopentane. Using the obtained N1,N5-di(p-toluenesulfonyl)-1,5-diaminopentane and N-(4-bromobutyl)phthalimide as Chain A and Chain B, respectively, N1,N5,N11,N15-tetra(p-toluenesulfonyl)-1,15-diamino-5,11-diazapentadecane (Compound 13b) was derived from the above Chain A and Chain B according to the known methods (Patent Documents 1 to 5 and References 6). Specifically, Compound 11b was synthesized, and then this Compound 11b was reacted with N$_2$H$_4$ in DMF at 70° C. for 1 day to obtain Compound 12b. The obtained Compound 12b was first treated with 2 N HCl at 70° C. for 1 hour, and then reacted with TsCl in pyridine in the presence of NEt$_3$ at room temperature for 4 hours to obtain Compound 13b.

Subsequently, a mixture of the above Compound 13b (0.186 g), anhydrous potassium carbonate (0.149 g) and bromoethane (40 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N11,N15-tetra(p-toluenesulfonyl)-1,15-d-i(ethylamino)-5,11-diazapentadecane (Compound 14b, 0.173 g, yield: 87%). The results of elementary analysis of Compound 14b are shown in Table 2 below, and the results of $^1$H-NMR and $^{13}$C-NMR of the same are shown in Table 4 below, respectively. The obtained Compound 14c (163 mg) was heated with phenol (0.334 g) in 33% HBr in acetic acid (13 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15b (see Scheme 3) as colorless powder.

Example 3.3

Synthesis of 1,16-di (ethylamino)-5,12-diazahexadecane HBr salt (15c)

Diaminohexane as a raw material was reacted with tosyl chloride to obtain N1,N6-di(p-toluenesulfonyl)-1,6-diaminohexane. Using the obtained N1,N6-di(p-toluenesulfonyl)-1,6-diaminohexane and N-(4-bromobutyl) phthalimide as Chain A and Chain B, respectively, N1,N5,N12,N16-tetra(p-toluenesulfonyl)-1,16-diamino-5,12-diazahexadecane (Compound 13c) was derived from the above Chain A and Chain B according to the known methods (Patent Documents 1 to 5 and References 6) Specifically, Compound 11c was synthesized, and then this Compound 11c was reacted with $N_2H_4$ in DMF at 70° C. for 1 day to obtain Compound 12c. The obtained Compound 12c was first treated with 2 N HCl at 70° C. for 1 hour, and then reacted with TsCl in pyridine in the presence of $NEt_3$ at room temperature for 4 hours to obtain Compound 13c.

Subsequently, a mixture of the above Compound 13c (0.208 g), anhydrous potassium carbonate (0.164) and bromoethane (44 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N12,N16-tetra(p-toluenesulfonyl)-1,16-di(ethylamino)-5,12-diazahexadecane (Compound 14c, 0.243 g, yield: 99%). The results of elementary analysis of Compound 14c are shown in Table 2 below, and the results of $^1$H-NMR and $^{13}$C-NMR of the same are shown in Table 4 below, respectively. The obtained Compound 14c (233 mg) was heated with phenol (0.471 g) in 33% HBr in acetic acid (13 ml) with stirring on an oil bath at 75° C. for 20hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15c (see Scheme 3) as colorless powder.

Example 3.4

Synthesis of 1,17-di(ethylamino)-5,13-diazaheptadecane HBr salt (15d) (Scheme 3)

Diaminoheptane as a raw material was reacted with tosyl chloride at room temperature for 3 hours to obtain, N1,N7-di(p-toluenesulfonyl)-1,7,-diaminopentane. Using the obtained N1,N7-di(p-toluenesulfonyl)-1,7-diaminoheptane and N-(4-bromobutyl)phthalimide as Chain A and Chain B, respectively, N1,N5,N13,N17-tetra(p-toluenesulfonyl)-1,17-diamino-5,13-diazaheptadecane (13d) was derived from the above Chain A and Chain B according to the known methods (Patent Documents 1 to 5 and References 6). Specifically, Compound 11d was synthesized, and then this Compound 11d was reacted with $N_2H_4$ in DMF at 70° C. for 1 day to obtain Compound 12d. The obtained Compound 12d was first treated with 2 N HCl at 70° C. for 1 hour, and then reacted with TsCl in pyridine in the presence of $NEt_3$ at room temperature for 4 hours to obtain Compound 13d.

Subsequently, a mixture of the above Compound 13d (0.160 g) anhydrous potassium carbonate (0.180 g) and bromoethane (38 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N13,N17-tetra(p-toluenesulfonyl)-1,17-di(ethylamino)-5,13-diazaheptadecane (Compound 14d, 0.152 g, yield: 89%). The results of elementary analysis of Compound 14e are shown in Table 2 below, and the results of $^1$H-NMR and $^{13}$C-NMR of the same are shown in Table 4 below, respectively. The obtained Compound 14d (142 mg) was heated with phenol (0.283 g) in 33% HBr in acetic acid (13ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15d (see Scheme 3) as colorless powder.

Example 3.5

Synthesis of 1, 18-di(ethylamino)-5,14-diazaoctadecane HBr salt (15e) (Scheme 3)

Diaminooctane as a raw material was reacted with tosyl chloride at room temperature for 3 hours to obtain N1,N8-di(p-toluenesulfonyl)-1,8-diaminooctane. Using the obtained N1,N8-di(p-toluenesulfonyl)-1,8-diaminooctane and N-(4-bromobutyl)phthalimide as Chain A and Chain B, respectively, N1,N5,N14,N18-tetra(p-toluenesulfonyl)-1,18 diamino-5,14-diazaoctadecane (Compound 13e) was derived from the above Chain A and Chain B according to the known methods (Patent Documents 1 to 5 and, References 6). Specifically, Compound 11e was synthesized, and then this Compound 11e was reacted with $N_2H_4$ in DMF at 70° C. for 1 day to obtain Compound 12e. The obtained Compound 12e was first treated with 2 N HCl at 70° C. for 1 hour, and then reacted with TsCl in pyridine in the presence of $NEt_3$ at room temperature for 4 hours to obtain Compound 13e.

Subsequently, a mixture of the above Compound 13e (0.177 g,), anhydrous potassium carbonate (0.135 g) and bromoethane (37 ml) was allowed to react in DMF (40 ml) at room temperature for 3 days with stirring, filtered, and then concentrated. A substance exhibiting Rf of 0.4 in TLC (Merck, Art. 5715, chloroform:acetone (95 :5 v/v) ) was collected by silica gel column chromatography (Merck, Art. 7734, 770–230 mesh) using chloroform:acetone (95:5 v/v) as a developing solvent to obtain N1,N5,N14,N18-tetra(p-toluenesulfonyl)-1,18-di(ethylamino)-5,14-diazaoctadecane (Compound 14e, 0.173 g, yield: 92%). The results of elementary analysis of Compound 14e are shown in Table 2 below, and the results of $^1$H-NMR and $^{13}$C-NMR of the same are shown in Table 5 below, respectively. The obtained Compound 14e (163 mg) was heated with phenol (0.320 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15e (see Scheme 3) as colorless powder.

Example 3.6

Synthesis of 1,19-di(ethylamino)-5,15-diazanonadecane HBr salt (1Sf) (Scheme 3)

Diaminononane as a raw material was reacted with tosyl chloride at room temperature for 3 hours to obtain N1,N9-di(p-toluenesulfonyl)-1,9-diaminononane. Using the obtained N1,N9-di(p-toluenesulfonyl)-1,9-diaminononane and N-(4-bromobutyl)phthalimide as Chain A and Chain B, respectively, N1,N5,N15,N19-tetra(p-toluenesulfonyl)-1,19-diamino-5,15-diazanonadecane (Compound 13f) was derived from the above Chain A and Chain B according to the known methods (Patent Documents 1 to 5 and References 6) Specifically, Compound 11f was synthesized, and then this Compound 11f was reacted with $N_2H_4$ in DMF at 70° C. for 1 day to obtain Compound 12f. The obtained Compound 12f was first treated with 2 N HCl at 70° C. for 1 hour, and then reacted with TsCl in pyridine in the presence of $NEt_3$ at room temperature for 4 hours to obtain Compound 13f.

Subsequently, a mixture of the above Compound 13f (0.168 g), anhydrous potassium carbonate (0.126 g) and bromoethane (34 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N15,N19-tetra(p-toluenesulfonyl)-1,19-di(ethylamino)-5,15-diazanonadecane (Compound 14f, 0.174 g, yield: 98%). The results of elementary analysis of Compound 14f are shown in Table 2 below, and the results of $^1$H-NMR and 13C-NMR of the same are shown in Table 5 below, respectively. The obtained Compound 14f (164 mg) was heated with phenol (0.320 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15f (see scheme 3) as colorless powder.

Example 3.7

Synthesis of 1,20-di(ethylamino)-5,16-diazaeicosane HBr salt (Compound 15) (Scheme 3)

Diaminodecane as a raw material was reacted with tosyl chloride at room temperature for 3 hours to obtain N1,N10-di(p-toluenesulfonyl)-1,10-diaminodecane. Using the obtained N1,N10-di(p-toluenesulfonyl)-1,10-diaminodecane and N-(4-bromobutyl)phthalimide as Chain A and Chain B, respectively, N1,N5,N16,N20-tetra(p-toluenesulfonyl)-1,20-diamino-5,16-diazaeicosane (Compound 13g) was derived from the above Chain A and Chain B according to the known methods (Patent Documents 1 to 5 and References 6). Specifically, Compound 11g was synthesized, and then this Compound 11g was reacted with $N_2H_4$ in DMF at 70° C. for 1 day to obtain Compound 12 g. The obtained Compound 12g was first treated with 2 N HCl at 70° C. for 1 hour, and then reacted with TsCl in pyridine in the presence of $NEt_3$ at room temperature for 4 hours to obtain Compound 13g.

Subsequently, a mixture of the above Compound 13g (0.170 g), anhydrous potassium carbonate (0.126 g) and bromoethane (34 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N16,N20-tetra(p-toluenesulfonyl)-1,20-di(ethylamino)-5,16-diazaeicosane (Compound 14g, 0.177 g, yield: 98%). The results of elementary analysis of Compound 14g are shown in Table 2 below, and the results of $^1$H-NMR and $^{13}$C-NMR of the same are shown in Table 5 below, respectively. The obtained Compound 14g (167 mg) was heated with phenol (0.318 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15 (see Scheme 3) as colorless powder.

Example 4

Synthesis of 1-ethylamino-8-amino-4-azaoctane HBr salt (Compound 18)

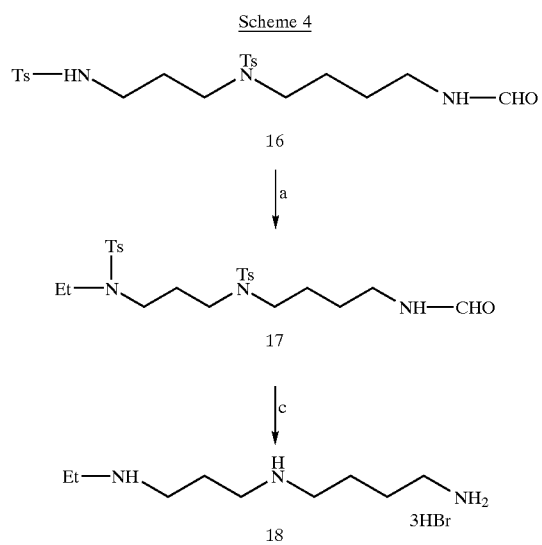

Scheme 4 a Et-Br/$K_2CO_3$/DMF, c 33%-HBr-AcOH

Using 4-bromobutylamine as a raw material, N-(p-toluenesulfonyl)-4-bromobutylamine was prepared by reacting it with tosylchloride at 0° C. for 1 hour. Subsequently, N-(p-toluenesulfonyl)-4-bromobutylamine was allowed to react with phthalimide at room temperature for 24hours to obtain N-(N4-p-toluenesulfonyl-4-aminobutyl)phthalimide. Using the obtained N-(N4-p-toluenesulfonyl-4-aminobutyl)phthalimide and N-(p-toluenesulfonyl-3-bromopuropil- amine as Chain A and Chain B, respectively, N1,N4-di(p-toluenesulfonyl)-N8-formyl-1,8-diamino-4-azaocta ne (Compound 18) was derived from the above Cain A and Chain B according to the publicly known method (Patent Documents 1 to 5and Reference 6). Specifically, Compound 11f was synthesized, and then this Compound 11f was reacted with $N_2H_4$ in DMF at 70° C. for one day to obtain Compound 12f. The obtained Compound 12f was first treated with 2N HCl at 70° C. for one hour, and then reacted with TsCl in pyridine in the presence of $NEt_3$ at room temperature for four hours to obtain Compound 13f.

Subsequently, a mixture of the above Compound 13f (0.236 g), anhydrous potassium carbonate (0.339 g) and bromoethane (91 ml) was allowed to react in DMF (50 ml) at room temperature for 3 days with stirring, filtered, and then concentrated. A substance exhibiting Rf of 0.3 in TLC (Merck, Art. 5715, chloroform:acetone (9:1 v/v)) was collected by silica gel column chromatography (Merck, Art. 7734, 70–230 mesh) using chloroform:acetone (7:3 v/v) as a developing solvent to obtain N1-ethyl-N1,N4-di(p-toluenesulfonyl)-N8-formyl-1,8-diamino-4-azaoctane (Compound 17, 0.221 g, yield: 88%). The results of elementary analysis of Compound 17 are shown in Table 2 below, and the results of $^1$H-NMR and $^{13}$C-NMR of the same are shown in Table 6 below, respectively. The obtained Compound 23 (210 mg) was heated with phenol (0.929 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 18 (see Scheme 4) as colorless powder Example 5

Synthesis of 1,18-diamino-5,14-diazaoctadecane HBr salt (Compound 19)

Scheme 5

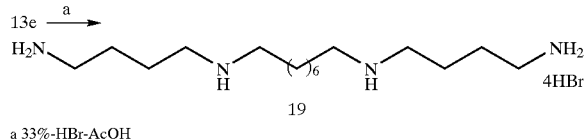

a 33%-HBr-AcOH

Compound 13e synthesized in Example 3.6 (152 mg) was heated with phenol (0.317 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 13e (see Scheme5) as colorless powder.

Example 6.1

Synthesis of N1,N8-di(p-toluenesulfonyl)-di (ethylamino)-octane (Compound 20) and N1,N8di (ethylamino)-octane (Compound 21) HBr salt Scheme 6

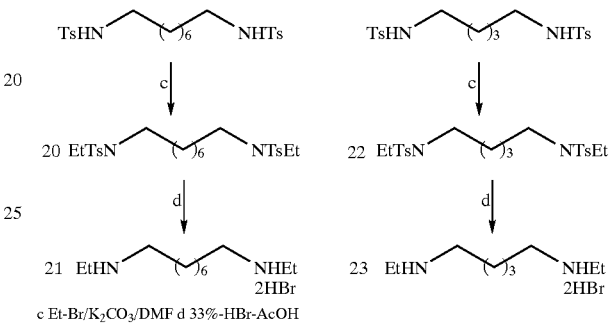

c Et-Br/$K_2CO_3$/DMF d 33%-HBr-AcOH

First, using 1,8-diaminooctane as a raw material, N1,N8-di(p-toluenesulfonyl)-1,8-diaminooctane was prepared according to the method described in M. Iwata and H. Kuzuhara, Bull. Chem. Soc. Jpn., 55, pp. 2153–2157 (1982).

Subsequently, a mixture of the above N1,N8-di(p-toluenesulfonyl)-1,8-diaminooctane (1.0 g) anhydrous potassium carbonate (1.54 g) and bromoethane (2.5 molar equivalents) was allowed to react in DMF (60ml) at room temperature for 3 days with stirring, filtered, and then concentrated. A substance exhibiting Rf of 0.7 in TLC (Merck, Art. 5715, chloroform:acetone (98:2 v/v)) was collected by silica gel column chromatography (Merck, Art. 7734, 70–230mesh) using chloroform:acetone (98:2 v/v) as a developing solvent to obtain N1,N8-di(p-toluenesulfonyl)-1,8-di(ethylamino)octane (Compound 20, 0.901 g, mp: 112–3° C. (recrystallized from a mixture of acetone and methanol)). The results of elementary analysis of Compound 20 are shown in Table 2 below, and the results of $^1$H-NMR and $^{13}$C-NMR of the same are shown in Table 5 below, respectively. The obtained Compound 20 (876 mg) was heated with phenol (20 molar equivalents) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21 (see Scheme 6) as colorless powder.

Example 6.2

Synthesis of N1,N5-di(p-toluenesulfonyl)-di(ethylamino)pentane (Compound 22) and N1,N5-di(ethylamino)pentane HBr salt (Compound 23)

First, using 1,5-diaminopentane as a raw material, N1,N5-di(p-toluenesulfonyl)-1,5-diaminopentane was prepared according to the method described in M. Iwata and H. Kuzuhara, Bull. Chem. Soc. Jpn., 55, pp. 2153–2157 (1982).

Subsequently, a mixture of the above N1,N5-di(p-toluenesulfonyl)-1,5-diaminopentane (1.0 g) anhydrous potassium carbonate (1.683 g) and bromoethane (0.454 ml) was allowed to react in DMF (40 ml) at room temperature for 3 days with stirring, filtered, and then concentrated. A substance exhibiting Rf of 0.7 in TLC (Merck, Art. 5715, chloroform:acetone (98:2 v/v)) was collected by silica gel column chromatography (Merck, Art. 7734, 70–230 mesh) using chloroform:acetone (98:2 v/v) as a developing solvent to obtain N1,N5-di(p-toluenesulfonyl)-1,5-di(ethylamino)pentane (Compound 22, 0.901 g, mp: 112–3° C. (recrystallized from a mixture of acetone and methanol)). The results of elementary analysis of Compound 22 are shown in Table 2 below, and the results of $^1$H-NMR and $^{13}$C-NMR of the same are shown in Table 5 below, respectively. The obtained Compound 22 (744 mg) was heated with phenol (20 molar equivalents) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 23 (see Scheme 6) as colorless powder.

Physicochemical Analysis

To characterize the compounds, physicochemical analyses using elementary analysis and $^1$H-NMR and $^{13}$C-NMR spectrum analyses were performed for precursors subjected to detosylation reaction. The results are shown in Tables 2 to 6. The yields of detosylation reaction in which detosylated compounds were obtained from the precursors are shown in Table 2.

The yields of detosylation reactions for deriving target compounds from the precursors are summarized in Table 3. The results of $^1$H-NMR and $^{13}$C-NMR spectrum analyses of the precursors which were subjected to detosylation reaction, are summarized in Table 4 to 6.

TABLE 2

Values of Elementary analysis of Ethylpolyamine N-pertosylates

| | 4 (58) $C_{42}H_{58}N_4S_4O_8$ | | 9 (65) $C_{32}H_{45}N_3S_3O_6$ | | 14a (65) $C_{44}H_{62}N_4S_4O_8$ | | 14b (87) $C_{45}H_{64}N_4S_4O_8$ | |
|---|---|---|---|---|---|---|---|---|
| (yield/%) | Found | Calcd | Found | Calcd | Found | Calcd | Found | Calcd |
| C/% | 57.46 | 57.64 | 58.61 | 57.89 | 58.43 | 58.51 | 58.75 | 58.92 |
| H/% | 6.60 | 6.68 | 6.88 | 6.83 | 6.89 | 6.92 | 6.97 | 7.03 |
| N/% | 6.39 | 6.40 | 6.32 | 6.33 | 6.18 | 6.20 | 6.08 | 6.11 |

| | 14c (99) $C_{46}H_{66}N_4S_4O_8$ | | 14d (89) $C_{47}H_{68}N_4S_4O_8$ | | 14e (92) $C_{48}H_{70}N_4S_4O_8$ | | 14f (98) $C_{49}H_{72}N_4S_4O_8$ | |
|---|---|---|---|---|---|---|---|---|
| (yield/%) | Found | Calcd | Found | Calcd | Found | Calcd | Found | Calcd |
| C/% | 59.24 | 59.33 | 59.66 | 59.72 | 59.98 | 60.09 | 60.28 | 60.46 |
| H/% | 7.07 | 7.14 | 7.27 | 7.25 | 7.30 | 7.35 | 7.42 | 7.46 |
| N/% | 5.98 | 6.02 | 6.01 | 5.93 | 5.85 | 5.84 | 5.74 | 5.76 |

| | 14g (98) $C_{50}H_{74}N_4S_4O_8$ | | 17 (88) $C_{24}H_{35}N_3S_2O_5$ | | 20 (80) $C_{26}H_{40}N_2S_2O_4$ | | 22 (72) $C_{23}H_{34}N_2S_2O_4$ | |
|---|---|---|---|---|---|---|---|---|
| (yield/%) | Found | Calcd | Found | Calcd | Found | Calcd | Found | Calcd |
| C/% | 60.94 | 60.82 | 56.57 | 56.56 | 61.35 | 61.38 | 59.12 | 59.20 |
| H/% | 7.59 | 7.55 | 6.97 | 6.92 | 7.95 | 7.93 | 7.38 | 7.34 |
| N/% | 5.60 | 5.67 | 7.99 | 8.24 | 5.45 | 5.51 | 5.93 | 6.00 |

TABLE 3

Yields of detosylation compounds

| Compnd | Yield/% |
|---|---|
| 5 | 87 |
| 10 | 91 |
| 15a | 91 |
| 15b | 88 |
| 15c | 89 |
| 15d | 91 |
| 15e | 85 |
| 15f | 89 |
| 15g | 90 |
| 18 | 91 |
| 19 | 94 |
| 21 | 96 |
| 23 | 95 |

TABLE 4

¹H- and ¹³C-NMR Spectral Data of Ethylpolyamine pertosylates (δ/ppm from TMS in CDCl₃, J/Hz)

| | ¹H-NMR | | | | | ¹³C-NMR | | | | |
|---|---|---|---|---|---|---|---|---|---|---|
| Compnd | Et | —(CH₂)₃— | —(CH₂)₂— | aromatic | aromatic | Et | —(CH₂)₃— | —(CH₂)₂— | aromatic | aromatic |
| 4 | 1.07, t | 1.86, quin | 1.58, m | 2.41, s | 7.31, d | 13.91 | 28.71 | 25.75 | 21.48 | 136.20 |
| | 3.19, quar | 3.11, t | 3.10, quin | 2.42, s | 7.66, d | 43.14 | 45.46 | 48.39 | 127.07 | 136.65 |
| | J=7.32 | 3.13, t | J=7.32 | 7.29, d | 7.67, d | | 46.51 | | 127.12 | 143.16 |
| | | J=7.32 | | J=8.30 | J=8.30 | | | | 129.69 | 143.31 |
| | | | | | | | | | 129.77 | |

| Compnd | Et | —(CH₂)₄— | —(CH₂)₃— | aromatic | aromatic | Et | —(CH₂)₄— | —(CH₂)₃— | aromatic | aromatic |
|---|---|---|---|---|---|---|---|---|---|---|
| 9 | 1.08, t | 1.57, m | 1.87, quin | 2.42, s | 7.31, d | 13.91 | 25.65 | 28.69 | 21.47 | 129.75 |
| | 1.09, t | 3.12, t | 3.13, t | 2.43, s | 7.67, d | 14.00 | 25.75 | 46.91 | 127.04 | 136.27 |
| | 3.18, quar | 3.12, t | 3.15, t | 7.29, d | 7.67, d | 42.84 | 45.44 | 48.40 | 127.07 | 136.66 |
| | 3.21, quar | J=7.32 | J=7.32 | 7.29, d | 7.68, d | 43.12 | 46.43 | | 127.12 | 136.98 |
| | J=7.32 | | | | J=8.30 | | | | 129.65 | 143.05 |
| | | | | | | | | | 129.69 | 143.18 |
| | | | | | | | | | | 143.31 |

| Compnd | Et | —(CH₂)₄— | —(CH₂)ₙ— | aromatic | aromatic | Et | —(CH₂)₄— | —(CH₂)ₙ— | aromatic | aromatic |
|---|---|---|---|---|---|---|---|---|---|---|
| 14a | 1.05, t | 1.55~1.57, m | 1.56, m | 2.41, s | 7.30, d | 13.96 | 25.73 | 25.94 | 21.48 | 136.63 |
| | 3.17, quar | 3.11~3.13, m | 3.10~3.13, m | 2.42, s | 7.67, d | 42.78 | 25.79 | 48.02 | 127.04 | 137.01 |
| | J=7.32 | | J=7.32 | 7.28, d | 7.68, d | | 46.94 | | 127.09 | 143.03 |
| | | | | J=8.30 | J=8.30 | | | | 129.64 | 143.18 |
| | | | | | | | | | 129.70 | |
| 14b | 1.05, t | 1.55~1.57, m | 1.26, quin | 2.41, s | 7.30, d | 13.98 | 25.73 | 23.80 | 21.47 | 136.68 |
| | 3.17, quar | 3.11~3.13, m | 1.53, m | 2.42, s | 7.67, d | 42.79 | 25.79 | 28.41 | 127.02 | 136.99 |
| | J=7.32 | | 3.06, t | 7.28, d | 7.68, d | | 46.97 | 48.42 | 127.07 | 143.03 |
| | | | J=7.32 | | J=8.30 | | 47.96 | | 129.64 | 143.13 |
| | | | | | | | | | 129.67 | |
| 14c | 1.06, t | 1.57~1.58, m | 1.26, quin | 2.41, s | 7.30, d | 14.00 | 25.75 | 26.30 | 21.47 | 136.76 |
| | 3.17, quar | 3.11, t | 1.50, quin | 2.42, s | 7.67, d | 42.79 | 25.79 | 28.71 | 127.04 | 137.01 |
| | J=7.32 | 3.12, t | 3.06, t | 7.28, d | J=8.30 | | 46.99 | 48.42 | 127.07 | 143.03 |
| | | J=7.32 | J=7.32 | J=8.30 | | | 47.83 | | 129.65 | 143.10 |
| 14d | 1.07, t | 1.57~1.58, m | 1.23, quin | 2.42, s | 7.30, d | 14.00 | 25.78 | 26.63 | 21.47 | 136.80 |
| | 3.17, quar | 3.11, t | 1.25, quin | 7.29, d | 7.67, d | 42.78 | 46.99 | 28.69 | 127.04 | 137.01 |
| | J=7.32 | 3.13, t | 1.50, quin | J=8.30 | J=8.30 | | 47.80 | 28.76 | 127.07 | 143.06 |

TABLE 5

| | ¹H-NMR | | | | | ¹³C-NMR | | | | |
|---|---|---|---|---|---|---|---|---|---|---|
| Compnd | Et | —(CH₂)₄— | —(CH₂)ₙ— | aromatic | aromatic | Et | —(CH₂)₄— | —(CH₂)ₙ— | aromatic | aromatic |
| | | J=7.32 | 3.06, t | | | | | 48.50 | 129.64 | |
| | | | J=7.32 | | | | | | | |
| 14e | 1.07, t | 1.58, m | 1.24, m | 2.42, s | 7.29, d | 14.01 | 25.75 | 26.63 | 21.47 | 136.83 |
| | 3.18, quar | 3.12, t | 1.50, quin | 7.29, d | 7.67, d | 42.78 | 25.78 | 28.72 | 127.04 | 137.01 |
| | J=7.32 | 3.13, t | 3.06, t | J=8.30 | J=8.30 | | 46.99 | 29.10 | 127.07 | 143.05 |
| | | J=7.32 | J=7.32 | | | | 47.74 | 48.50 | 129.64 | |
| 14f | 1.07, t | 1.57, m | 1.23, m | 2.42, s | | 14.01 | 25.75 | 26.72 | 21.47 | 136.84 |
| | 3.18, quar | 3.12, t | 1.49, quin | 7.29, d | | 42.78 | 25.78 | 28.74 | 127.04 | 137.01 |
| | J=7.32 | 3.13, t | 3.06, t | 7.67, d | | | 46.99 | 29.10 | 127.07 | 143.03 |
| | | J=7.32 | J=7.32 | J=8.30 | | | 47.71 | 29.43 | 129.62 | |
| | | | | | | | | 48.50 | | |
| 14g | 1.07, t | 1.57, m | 1.23, m | 2.42, s | | 14.01 | 25.76 | 26.75 | 21.47 | 136.86 |
| | 3.18, quar | 3.12, t | 1.49, quin | 7.29, d | | 42.78 | 46.99 | 28.72 | 127.04 | 137.03 |
| | J=7.32 | 3.13, t | 3.06, t | 7.68, d | | | 47.70 | 29.17 | 127.07 | 143.03 |
| | | J=7.32 | J=7.32 | J=8.30 | | | | 29.43 | 129.64 | |
| | | | | | | | | 48.50 | | |
| 20 | 1.10, t | | 1.26, m | 2.42, s | | 14.06 | | 26.55 | 21.45 | 142.88 |
| | 3.20, quar | | 1.52, quin | 7.29, d | | 42.59 | | 28.67 | 127.04 | |
| | J=7.32 | | 3.10, t | 7.68, d | | | | 29.09 | 129.55 | |
| | | | J=7.32 | J=8.30 | | | | 47.51 | 137.24 | |
| 22 | 1.09, t | | 1.32, quin | 2.42, s | | 14.01 | | 23.67 | 21.47 | 142.98 |
| | 3.20, quar | | 1.57, quin | 7.29, d | | 42.76 | | 28.39 | 127.04 | |
| | J=7.32 | | 3.10, t | 7.63, d | | | | 47.37 | 129.60 | |
| | | | J=7.32 | J=8.30 | | | | | 137.09 | |

TABLE 6

| Compnd | ¹H-NMR | | | | | ¹³C-NMR | | | | |
|---|---|---|---|---|---|---|---|---|---|---|
| | Et | —(CH₂)₄— | —(CH₂)₃— | NH—CHO/aromatic | | Et | —(CH₂)₄— | —(CH₂)₃— | NH—CHO/aromatic | |
| 17 | 1.07, t | 1.60, quin | 1.86, quin | 2.43, s | 7.66, d | 13.91 | 26.39 | 28.23 | 21.48 | 136.37 |
| | 3.19, quar | 1.67, quin | 3.14, t | 6.05, bs | 7.67, d | 43.40 | 37.36 | 45.54 | 127.04 | 143.39 |
| | J=7.32 | 3.10, t | 3.18, t | 7.31, d | 8.16, bs | | | 49.08 | 46.92 | 127.12 | 143.43 |
| | | 3.34, quar | J=7.32 | J=8.30 | J=8.30 | | | | | 129.77 | 161.44 |
| | | J=7.32 | | | | | | | | 135.91 | |

Example 7

Evaluation Method for Accelerating Effect on RNA Polymerase Transcription Activity An activation level was evaluated by observing an effect of a polyamine on in vitro transcription activation using bacteriophage T7 RNA polymerase in the reaction system below.

Each polyamine was added to 10 μl of reaction solution (40 mM Tris-Cl, pH 8.0, 8 mM MgCl₂, 5 mM DTT, 200 M GMP, wild-type T7 RNA polymerase 5U, 0.2 μCi [α32P] UTP, dsDNA produced by cleavage of pBluescript [Stratagene] by a restriction enzyme PvuII 500 μM as rNTP template DNA) to yield a final concentration of 2 mM, then reacted at 37° C. for one hour. After the reaction, 10 μl of formamide loading dye (98% formamide, 10 mM EDTA) was added to the products, heated at 90° C. for modification, subsequently analyzed by electrophoresis on 4% acrylamide gel. The gel was dried after the electrophoresis, observed for radioactivity contained in the transcription products using the BAS2000 image analysis system (Fujiphotofilm Inc.), and evaluated for activation level of each polyamine.

The results are shown in Table 7. Data is given in amplification of radioactivity compared to a blank in which a reaction is carried out in parallel in the same condition excepting no polyamine was added.

TABLE 7

Accelerating effect of synthetic polyamines on transcription activity of T7 RNA polymerase

| No. | Com-pound | Characteristics | Molecular Formula | Molecular Weight | Activity Level [a] |
|---|---|---|---|---|---|
| 1. | 5 | BET - 343/HBr | C₁₄H₃₄N₄4HBr | 582.101 | 1.01 |
| 2. | 10 | BET - 43/HBr | C₁₁H₂₇N₃3HBr | 444.093 | 3.05 |
| 3. | 15a | BET - 444/HBr | C₁₆H₃₈N₄4HBr | 610.155 | 1.21 |
| 4. | 15b | BET - 454/HBr | C₁₇H₄₀N₄4HBr | 624.182 | 1.18 |
| 5. | 15c | BET - 464/HBr | C₁₈H₄₂N₄4HBr | 638.209 | 1.12 |
| 6. | 15d | BET - 474/HBr | C₁₉H₄₄N₄4HBr | 652.236 | 1.29 |
| 7. | 15e | BET - 484/HBr | C₂₀H₄₆N₄4HBr | 666.263 | 2.52 |
| 8. | 15f | BET - 494/HBr | C₂₁H₄₈N₄4HBr | 680.290 | 1.18 |
| 9. | 15g | BET - 4104/HBr | C₂₂H₅₀N₄4HBr | 694.316 | 2.01 |
| 10. | 18 | ET34/HBr | C₉H₃N₃3HBr | 416.039 | 1.12 |
| 11. | 19 | 484/HBr | C₁₆H₃₈N₄4HBr | 610.155 | 1.41 |
| 12. | 20 | BET - 8/Ts | C₂₆H₄₀N₂O₄S₂ | 508.751 | 1.11 |
| 13. | 21 | BET - 8/HBr | C₁₂H₂₈N₂2HBr | 362.193 | 4.91 |
| 14. | 22 | BET - 5/Ts | C₂₃H₃₄N₂O₄S₂ | 466.670 | 1.43 |
| 15. | 23 | BET - 5/HBr | C₉H₂₂N₂2HBr | 320.112 | 3.52 |

Activity level [a] is shown in a rate against transcription activity when enzyme is not added.

It has been revealed that ethylated amine compounds have much stronger accelerating effect than the original amine compound from comparison between Compounds 10 and 18, and Compounds 15e and 19.

It has been also revealed that a tosyl group which is one of substituents suppressing transcription activity of RNAP from comparison between Compounds 20 and 21, and Compounds 22 and 23.

A difference of activity levels of tetramine 5 and Compound 15a is thought to reflect a difference in the length of methylene chain on the both ends. Taking the length of methylene chains at the both ends into an account, tetramethylene shows better transcription activity accelerating effect than trimethylene.

Remarkable chain length specificity can be observed in an influencing on the transcription activity accelerating effect which results from a difference in methylene chain length in a center of a tetramine. A compound with octamethylene or decamethylene shows about twofold increase in transcription activity accelerating effect compared to that of the other compounds.

Sequencing of DNA with a longer strand becomes possible by addition of the transcription promoter of the present invention even if the amount of RNA polymerase used for DNA sequencing method is not increased. Further, the amount of RNA polymerase or a template used in the nucleic acid transcription reaction can be reduced by the use of the compound of the present invention when the lengths of the DNAs to be subjected are not to be elongated.

What is claimed is:

1. A method for sequencing DNA in which nucleic acid transcripts are produced by using RNA polymerase and a DNA fragment as a template, the resulting nucleic acid transcripts are separated into fractions, and the nucleic acid sequence is determined from the separated fractions, wherein said nucleic acid transcripts are produced in the presence of at least one compound represented by the following Formula (I), or salts thereof,

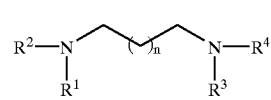

(I)

wherein n is an integer of 1–7, $R^1$ represents a hydrogen atom or a p-toluenesulfonyl group, $R^2$ represents an ethyl group or a group represented by the following Formula (II), $R^3$ represents a hydrogen atom or a p-toluenesulfonyl group, and $R^4$ represents an ethyl group or a group represented by the following Formula (II):

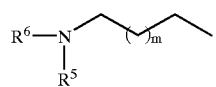 (II)

wherein
m is 1 or 2,
$R^5$ represents a hydrogen atom, and
$R^6$ represents a hydrogen atom or an ethyl group.

2. The method of claim 1 wherein said DNA fragment comprises a promoter sequence for the RNA polymerase, and the nucleic acid transcripts are produced using ribonucleoside-5'-triphosphates comprising ATP, GTP, CTP and UTP or derivatives thereof, and one or more kinds of 3'-deoxyribonucleoside-5'-triphosphate (hereinafter referred to as 3' dNTP derivatives) comprising 3' dATP, 3' dGTP, 3' dCTP, 3' dUTP and derivatives thereof.

3. The method of claim 2 wherein the 3' dNTP derivatives are labeled, and nucleic acid sequence is determined using the label.

* * * * *